(12) United States Patent
Olson et al.

(10) Patent No.: US 9,652,594 B2
(45) Date of Patent: *May 16, 2017

(54) MEDICATION STORAGE AND DISPENSING APPARATUS HAVING LINEAR DRAWER ASSEMBLY INCLUDING DISCRETE STORAGE MODULES

(71) Applicant: TOUCHPOINT MEDICAL, INC., Concordville, PA (US)

(72) Inventors: Jeffrey C. Olson, Wilkes-Barre, PA (US); Scott Curtis Miller, Wilkes-Barre, PA (US); James Leo Kilgallon, Wilkes-Barre, PA (US); Tobin H. Williams, Wilkes-Barre, PA (US); Paul Prickett, Wilkes-Barre, PA (US); Karl Haiden, Wilkes-Barre, PA (US); Scott Harshbarger, Wilkes-Barre, PA (US); Adam Troup, Wilkes-Barre, PA (US); Patrick Sweeney, Wilkes-Barre, PA (US)

(73) Assignee: TOUCHPOINT MEDICAL, INC., Concordville, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/775,392

(22) PCT Filed: Mar. 14, 2014

(86) PCT No.: PCT/US2014/027940
§ 371 (c)(1),
(2) Date: Sep. 11, 2015

(87) PCT Pub. No.: WO2014/143810
PCT Pub. Date: Sep. 18, 2014

(65) Prior Publication Data
US 2016/0019367 A1    Jan. 21, 2016

Related U.S. Application Data

(60) Provisional application No. 61/793,325, filed on Mar. 15, 2013.

(51) Int. Cl.
*G06F 19/00* (2011.01)
*G07F 11/62* (2006.01)
(Continued)

(52) U.S. Cl.
CPC .......... *G06F 19/3462* (2013.01); *A47B 67/02* (2013.01); *A47B 81/00* (2013.01);
(Continued)

(58) Field of Classification Search
CPC ..... G07F 17/0092; G07F 11/62; A47B 87/00; A61J 7/04
(Continued)

(56) References Cited

U.S. PATENT DOCUMENTS 3,970,010 A    7/1976   Cantley
5,172,829 A   12/1992   Dellicker, Jr.
(Continued)

FOREIGN PATENT DOCUMENTS

EP         1086442      3/2001
WO    WO-9905943 A1    2/1999

OTHER PUBLICATIONS

International Search Report and Written Opinion for PCT/US2014/027940, mailed Aug. 20, 2014; ISA/US.
(Continued)

*Primary Examiner* — Timothy Waggoner
(74) *Attorney, Agent, or Firm* — RatnerPrestia

(57) ABSTRACT

A medication storage and dispensing workstation for use in a medication management system administering the inventory and distribution of pharmaceuticals and medical sup-
(Continued)

plies in a healthcare environment is disclosed. The workstation incorporates a linear drawer assembly having a plurality of discrete, removable, storage modules for containing medications and/or other medical supplies. The storage modules are arranged in a linear array extending longitudinally along the travel path of the linear drawer assembly. Each storage module, in turn, comprises a drawer that is extensible laterally relative to the linear arrangement of the storage modules. As such, the drawer assemblies comprise a compartmentalized "drawer-in-drawer" arrangement that provides an efficient use of storage space and enables a user to utilize the workstation in a workspace having a smaller footprint that traditional storage cabinet apparatus.

34 Claims, 14 Drawing Sheets

(51) Int. Cl.

| | | |
|---|---|---|
| *G07F 17/00* | (2006.01) | |
| *A47B 67/02* | (2006.01) | |
| *A47B 81/00* | (2006.01) | |
| *A61J 7/00* | (2006.01) | |
| *E05B 65/46* | (2017.01) | |
| *G05B 15/02* | (2006.01) | |
| *G07F 11/18* | (2006.01) | |
| *A47B 88/40* | (2017.01) | |

(52) U.S. Cl.
CPC ............ *A47B 88/40* (2017.01); *A61J 7/0069* (2013.01); *A61J 7/0084* (2013.01); *E05B 65/46* (2013.01); *G05B 15/02* (2013.01); *G07F 11/18* (2013.01); *G07F 11/62* (2013.01); *G07F 17/0092* (2013.01); *A47B 2067/025* (2013.01); *A61J 2205/10* (2013.01); *A61J 2205/20* (2013.01); *A61J 2205/60* (2013.01)

(58) Field of Classification Search
USPC .................. 312/298, 301, 330.1; 700/242
See application file for complete search history.

(56) References Cited

U.S. PATENT DOCUMENTS

| | | |
|---|---|---|
| 5,392,951 A | 2/1995 | Gardner et al. |
| 5,745,366 A | 4/1998 | Higham et al. |
| 5,805,456 A | 9/1998 | Higham et al. |
| 5,883,806 A | 3/1999 | Meador et al. |
| 5,905,653 A | 5/1999 | Higham et al. |
| 6,011,999 A | 1/2000 | Holmes |
| 6,039,467 A | 3/2000 | Holmes |
| 6,116,461 A | 9/2000 | Broadfield et al. |
| 6,209,978 B1 | 4/2001 | Khan |
| 6,338,007 B1 | 1/2002 | Broadfield et al. |
| 6,349,999 B1 | 2/2002 | Takahashi et al. |
| 6,470,234 B1 | 10/2002 | McGrady |
| 6,648,428 B2 | 11/2003 | Chaloner et al. |
| 6,698,634 B2 | 3/2004 | Thomson |
| 6,785,589 B2 | 8/2004 | Eggenberger et al. |
| 7,263,410 B1 | 8/2007 | Frederick et al. |
| 7,719,420 B2 | 5/2010 | Christie et al. |
| 7,751,932 B1 | 7/2010 | Fedor et al. |
| 7,806,488 B2 | 10/2010 | Hannan et al. |
| 8,016,370 B2 | 9/2011 | Grainger |
| 8,103,379 B2 | 1/2012 | Biba et al. |
| 8,831,770 B2 | 9/2014 | Heffron |
| 9,081,887 B2 * | 7/2015 | Olson ................ G07F 17/0092 |
| 2007/0235397 A1 | 10/2007 | Wannop |
| 2009/0108016 A1 | 4/2009 | Brown et al. |
| 2010/0256800 A1 | 10/2010 | Heffron |
| 2011/0030034 A1 | 2/2011 | Ross |
| 2011/0101018 A1 | 5/2011 | Shafir |
| 2011/0140831 A1 | 6/2011 | Michael |
| 2011/0245963 A1 | 10/2011 | Leng |
| 2012/0004772 A1 | 1/2012 | Rahilly et al. |
| 2012/0089248 A1 | 4/2012 | Biba et al. |
| 2012/0253510 A1 | 10/2012 | Thomas et al. |
| 2014/0277709 A1 | 9/2014 | Olson et al. |

OTHER PUBLICATIONS

International Preliminary Report on Patentability with Annex of Claims amended under PCT Article 34, IPEA/US, mailed Feb. 18, 2015.
Extended European Search Report for European Application No. 14764491.8, dated Nov. 29, 2016, 8 pages.
U.S. Appl. No. 14/796,085, filed Jul. 10, 2015, Jeffrey C. Olson et al.
U.S. Appl. No. 14/385,118, filed Sep. 18, 2014, Jeffrey C. Olson.

* cited by examiner

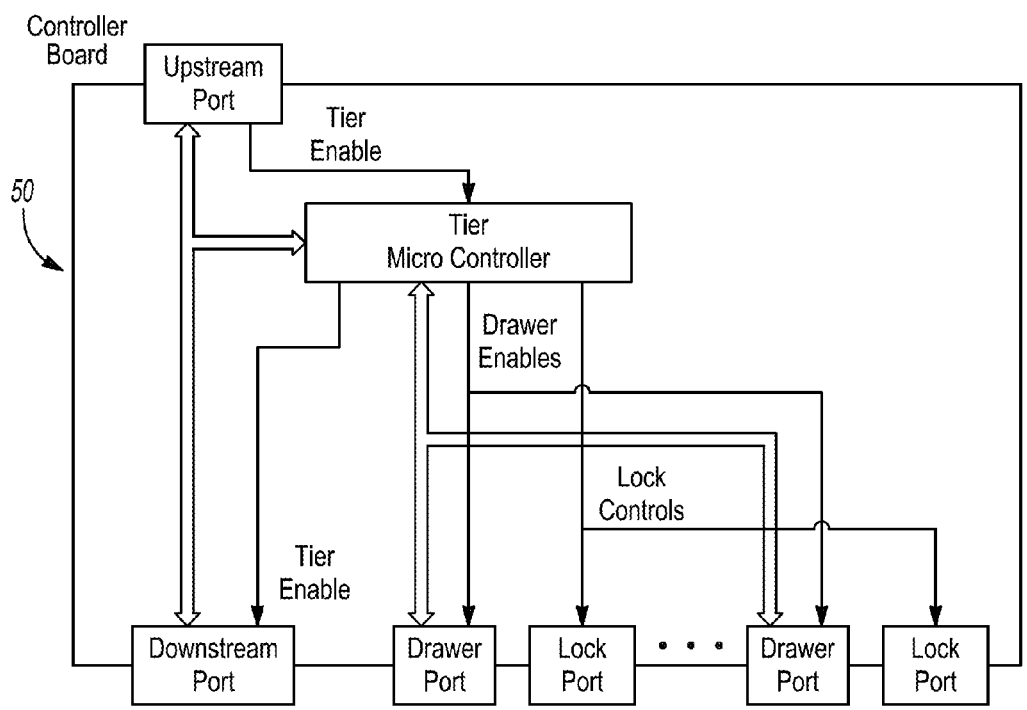

MEDICATION STORAGE AND DISPENSING APPARATUS HAVING LINEAR DRAWER ASSEMBLY INCLUDING DISCRETE STORAGE MODULES

CROSS-REFERENCE TO RELATED APPLICATIONS

This application is a National Phase of PCT/US2014/027940, filed on Mar. 14, 2014 and published in English as WO 2014/143810 A1 on Sep. 18, 2014, which claims the benefit of U.S. Provisional Application No. 61/793,325, filed on Mar. 15, 2013. The entire disclosures of the above applications are incorporated herein by reference.

FIELD

The present disclosure relates to medication management systems incorporating medication storage and dispensing workstations. In particular, the disclosure relates to medication storage and dispensing workstations comprising linear drawers having discrete and removable storage modules.

BACKGROUND

This section provides background information related to the present disclosure which is not necessarily prior art.

Medication management systems are used in healthcare environments in order to administer the inventory and distribution of medication and other medical supplies to patients. A decentralized unit dose medication dispensing system involves dispensing medications in the patient care areas. Medications are retrieved, e.g., from a medication storage and dispensing workstation, and placed in patient specific containers, transported to the patient care area and administered as prescribed. In addition to hospitals, decentralized medication management systems are used in long term care facilities, clinics, and in other medical environments. In a decentralized medication distribution system, multiple medication dispensing sites are located remotely from a centralized distribution location, such as a facility's pharmacy. The remote dispensing sites, such as a nurses' station in a hospital ward, serve as base stations from which healthcare professionals can readily access medications or other medical supplies to be administered to the patients under their care.

A medication storage and dispensing workstation can comprise a cabinet having a plurality of storage locations, such as drawers, shelves, trays, cassettes, or bins, for example. The storage locations are stocked with individual medications and/or medication doses, or other medical supplies by the pharmacy. The contents of the base stations are thoroughly inventoried and the distribution of medications and medical supplies is carefully controlled. Access to the medication storage and dispensing workstation and to the individual storage locations in the workstation, is limited and can be gained only by healthcare professionals with the appropriate credentials. A user interface that enables access to the workstation and records the inventory and distribution of the medications and medical supplies from the workstation can be computer controlled.

SUMMARY

This section provides a general summary of the disclosure, and is not a comprehensive disclosure of its full scope or all of its features.

The present disclosure provides a medication storage and dispensing workstation for use in a medication management system administering the inventory and distribution of pharmaceuticals and medical supplies in a healthcare environment. The workstation incorporates a linear drawer assembly having a plurality of discrete, removable, storage modules for containing medications and/or other medical supplies. The storage modules are arranged in a linear array extending longitudinally along the travel path of the linear drawer assembly. Each storage module, in turn, comprises a drawer that is extensible laterally relative to the linear arrangement of the storage modules.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a schematic block diagram showing a cabinet controller for use with a medication storage and dispensing workstation of the present disclosure;

FIG. 8 is a schematic block diagram showing a tier controller for use with a medication storage and dispensing workstation of the present disclosure;

Corresponding reference numerals indicate corresponding parts throughout the several views of the drawings.

DETAILED DESCRIPTION

Figure 1B:
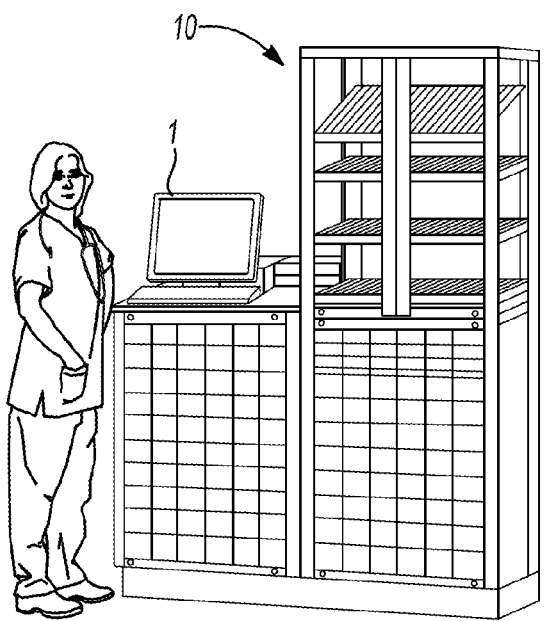
FIG. 1B is a front perspective view of an exemplary drawer assembly with storage modules according to the present disclosure.

Example embodiments will now be described more fully with reference to the accompanying drawings.

Referring now to the drawings, FIGS. 1-4 illustrate several exemplary medication storage and dispensing workstations suitable for use in a medication management system administering the inventory and distribution of pharmaceuticals and medical supplies in a healthcare environment. The workstations can incorporate discrete, drawer-in-drawer storage modules according to the present disclosure.

The workstations can take several forms, including stationary or mobile cabinets, such as automated dispensing machines ("ADMs"), and/or point-of-care (POC) mobile workstations. The workstations can be utilized in any of a variety of medication inventory and distribution models, including centralized, decentralized, local, and mobile distribution models, and generally in areas geared toward acute or long-term patient care. Of course, the workstations can also be employed in other inventory management environments outside of the healthcare field, as well.

Access to the workstation is limited to properly credentialed healthcare professionals by facility protocols. A healthcare professional may gain access to the medication storage modules of the workstation according to established protocols of the facility. Once access is obtained, the healthcare professional can retrieve medication(s) or other medical supplies from the workstation as they are needed or in order to fulfill the prescription requirements of individual patients which are under the healthcare professional's care.

Figure 1A:
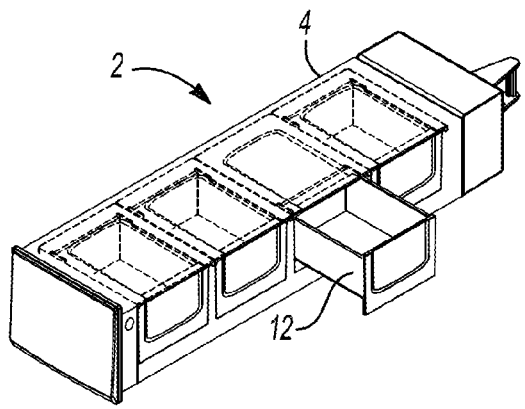
FIG. 1A is a front perspective view of an exemplary stationary medication storage and dispensing workstation incorporating discrete drawer-in-drawer storage modules according to the present disclosure.

FIG. 1A shows an exemplary stationary medication storage and dispensing workstation 10 for use in a healthcare environment. The workstation 10 includes one or more storage cabinets housing a plurality of drawers, and/or shelves that are located behind cabinet doors. A computer 1 operating under the direction of a medication inventory management software application program provides a user interface and controls access to and operation of the workstation 10.

The computer 1 can also enable networking the workstation 10 with other workstations and/or a centralized medication inventory management system. In this respect, the computer can comprise a wired network interface, e.g., an Ethernet adaptor for wired network connectivity to a local area network, or a wireless network interface and an antenna for network connectivity to a WLAN. Wired and wireless network interfaces that are well known in the art are suitable for integration into or with the computer of medication storage and dispensing workstation. Alternatively, or in addition, wireless signals at a frequency (or according to a protocol) other than the WLAN, such as Bluetooth, WiMAX, for example, can be used.

The computer 1 and/or application program can communicate with peripheral devices, such as bar code readers, PDAs, biometric security devices (e.g., a fingerprint scanner), scanners, card readers, keyboards, and the like. The computer 1 and/or application program can incorporate a healthcare facility's operating protocols for managing the distribution of medications and medical supplies and can be operable to access pertinent data, such as patient-specific prescription information, from a centralized medication inventory management system.

Shown in FIG. 1B is an exemplary drawer for use in the workstation 10 of the present disclosure. As further described herein, and as shown in the figures, particularly at FIGS. 10-12, 20 and 21, the drawer comprises a linear drawer assembly 2 that incorporates a plurality of discrete, removable, storage modules 4 for containing medications and/or other medical supplies. The storage modules 4 are arranged in a linear array extending longitudinally along the travel path of the linear drawer assembly 2. Each storage module 4, in turn, comprises a drawer 12 that is extensible laterally relative to the linear arrangement of the storage modules 4. As such, the drawer assemblies 2 comprise a compartmentalized "drawer-in-drawer" arrangement that provides an efficient use of storage space and enables a user to utilize the workstation 10 in a workspace having a smaller footprint than traditional storage cabinet apparatus.

Figure 2:
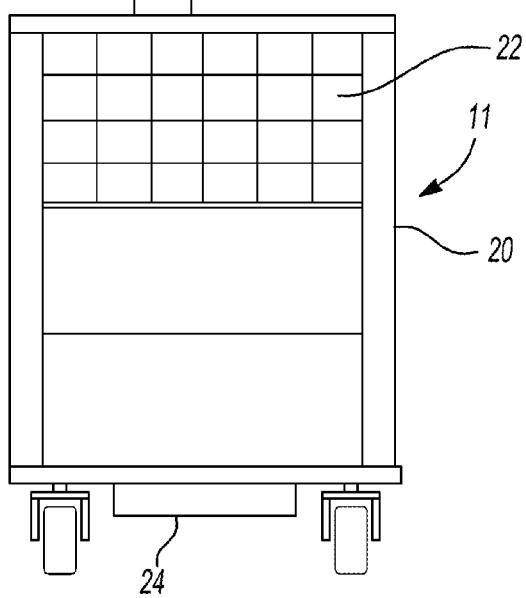
FIG. 2 is a front view of an exemplary mobile medication storage and dispensing workstation incorporating discrete drawer-in-drawer storage modules according to the present disclosure.
Figure 3:
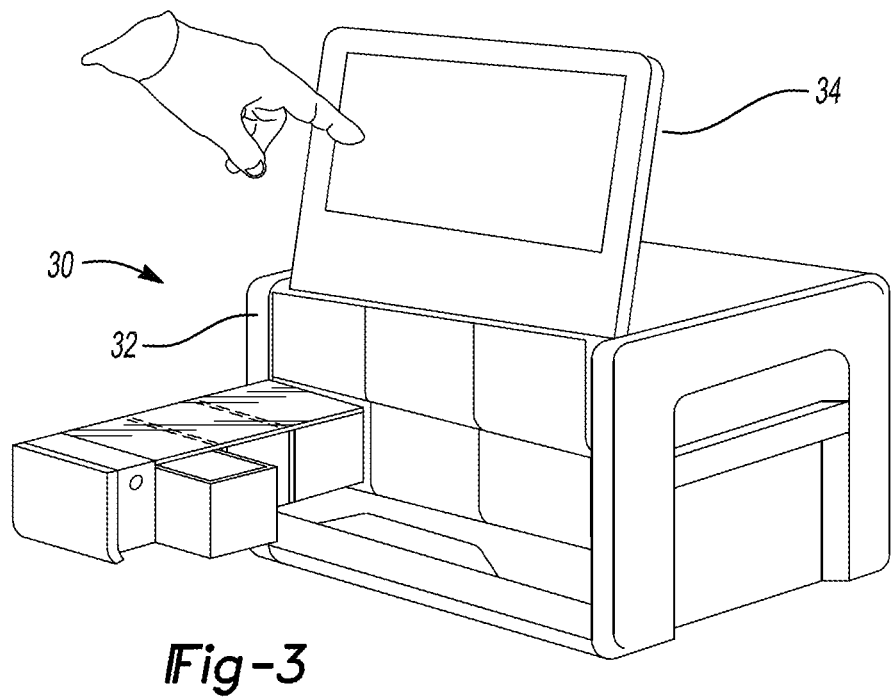
FIG. 3 is a front perspective view of an exemplary satellite medication storage and dispensing workstation incorporating discrete drawer-in-drawer storage modules according to the present disclosure.
Figure 4:
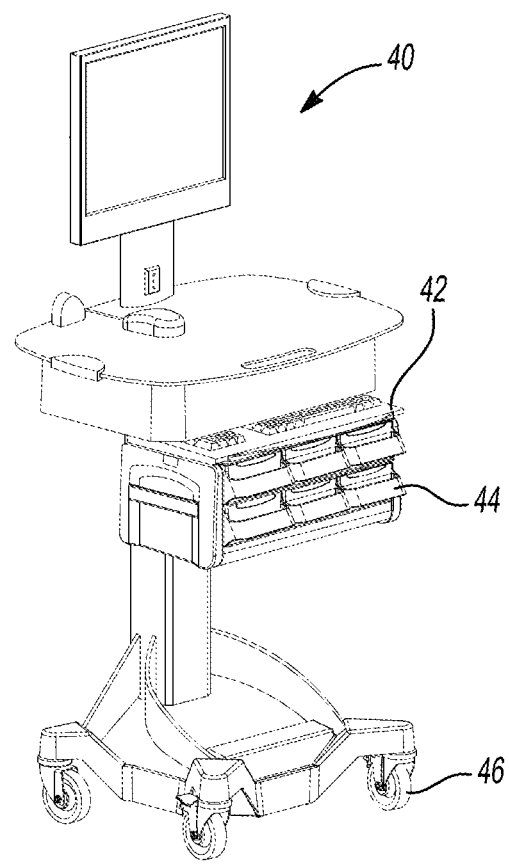
FIG. 4 shows a front perspective view of a mobile point of care (POC) workstation and a storage module for use the workstation incorporating discrete drawer-in-drawer storage modules according to the present disclosure.

FIGS. 2-4 illustrate additional exemplary storage and dispensing workstations according to the present disclosure that can include a linear drawer assembly that incorporates a plurality of discrete, removable, storage modules for containing medications and/or other medical supplies. FIG. 2 shows a mobile storage and dispensing workstation 11 comprising a storage cabinet 20 housing a plurality of drawers 22 and having a wheeled chassis 24 that enables the cabinet 20 to be easily moved from one location to another. A computer 26 operating under the direction of a medication inventory management software application program provides a user interface and controls access to and operation of the workstation 11. In FIG. 3, a scaled-down storage and dispensing workstation 30 is shown. The workstation 30 shown in FIG. 3 comprises a desktop sized cabinet 32 that is suitable to be located in or near a patient's room or bedside, for example. As such, the workstation 30 can serve as a "satellite" storage and dispensing device for patient-specific medications and/or medical supplies. The workstation 30 of FIG. 3 can be conveniently wall-mounted for easy access. A computer 34, such as a touch screen tablet device, can operate under the control medication inventory management software and provide a user interface and control access to and operation of the workstation 30. FIG. 4 illustrates a POC mobile workstation 40 that provides a mobile work platform 42 and includes a storage area 44 positioned beneath a work platform 42. The storage area 44 includes a plurality of linear drawer assemblies 2 with storage modules 4 according to the present disclosure and a wheeled chassis 46 that enables the workstation 40 to move from location to location. The POC mobile workstation 40 can serve as a mobile storage and dispensing device to serve the specific medication and/or medical supply needs for multiple patients. All of the foregoing workstations can incorporate the discrete, drawer-in-drawer storage modules according to the present disclosure.

Turning now generally to FIGS. 10-18, a linear drawer assembly incorporating the discrete, removable storage modules according to the present disclosure is illustrated. The linear drawer assembly includes a plurality of discrete storage modules sometimes referred to as "pods." The storage modules are arranged adjacent to one another in a linear array along a longitudinal axis of the linear drawer assembly. The storage modules are individually removable from the linear drawer assembly (see, e.g., FIG. 22) and can be easily replaced.

Figure 10A:
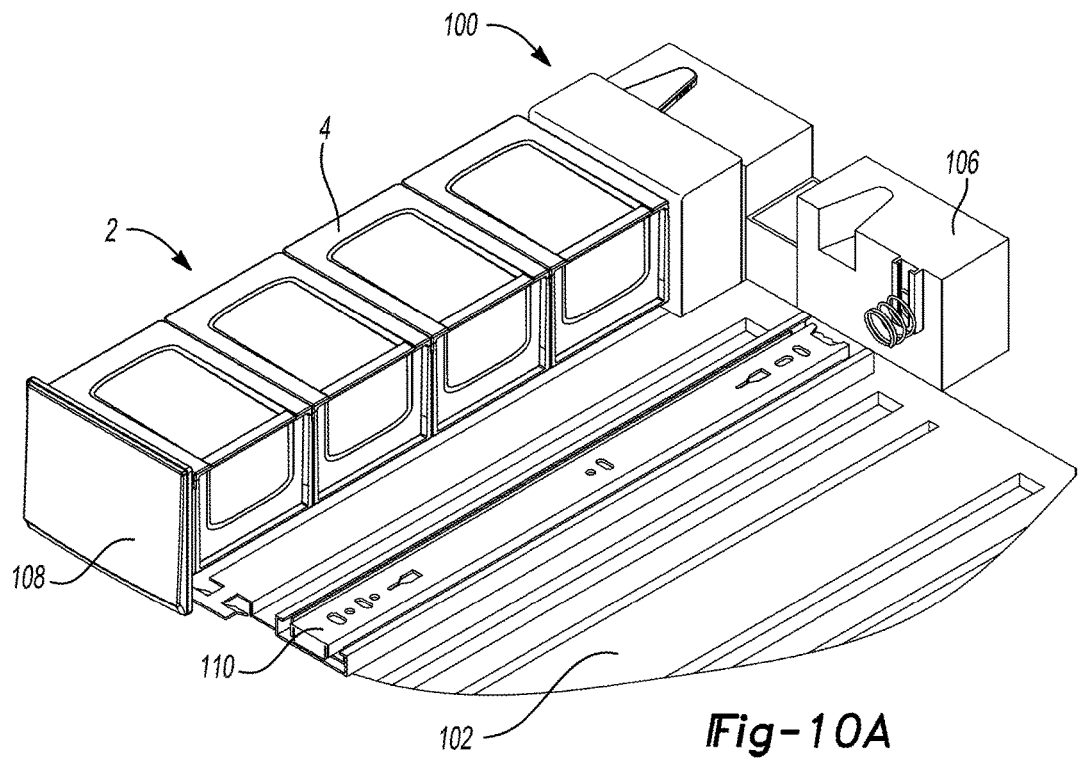
FIG. 10A is a front perspective view of a drawer assembly and a drawer frame for a medication storage and dispensing workstation incorporating discrete drawer-in-drawer storage modules according to the present disclosure.
Figure 10B:
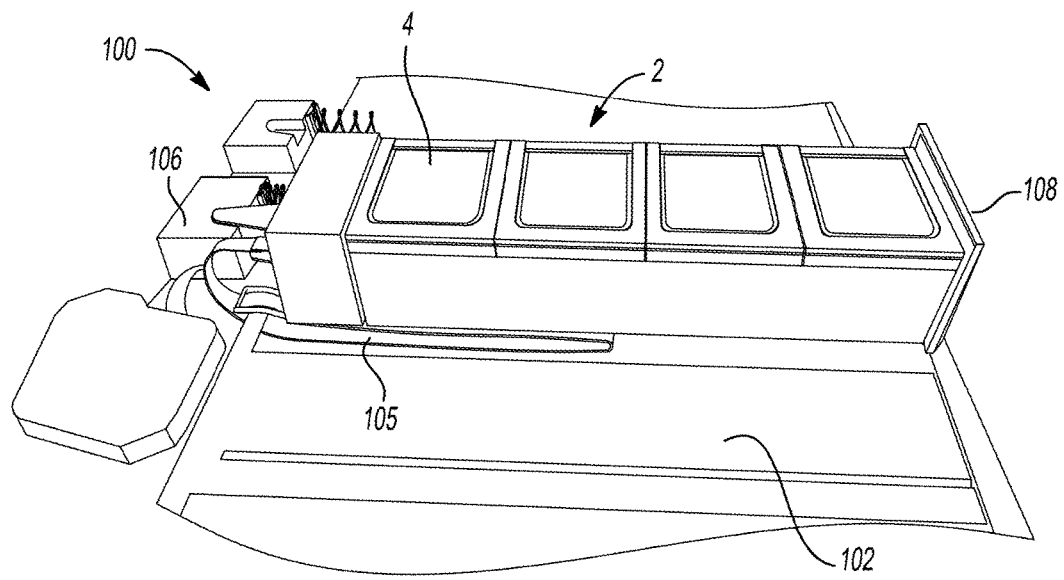
FIG. 10B is a side perspective view of a drawer assembly and a drawer frame for a medication storage and dispensing workstation incorporating discrete drawer-in-drawer storage modules according to the present disclosure.

As FIGS. 10A and 10B illustrate, an exemplary linear drawer assembly 2 is installed on a drawer tray 100 that is housed within, e.g., a cabinet portion of a medication storage and dispensing workstation. In FIG. 10A the linear drawer assembly 2 is depicted in a closed condition. The drawer tray 100 includes a plurality of mounting locations 102 for a corresponding plurality of linear drawer assemblies 2. Located at an interior back end of the drawer tray 100 are a corresponding plurality of linear drawer latch mechanisms 106. As shown, in the closed condition the linear drawer assembly 2 engages a corresponding linear drawer latch mechanism 106 and the linear drawer assembly 2 extends from the interior end of the drawer tray 100 to an exterior front end of the drawer tray. An aesthetic end cover 108 is included at the exposed end of the linear drawer assembly 2.

In certain embodiments, a communicative cable 105 is secured to the linear drawer assembly 2. The communicative cable 105 allows the linear drawer assembly 2 and its components to communicate generally with a control computer 54, cabinet controller 58, tier controller 50, in-drawer controller 56, and storage module controller 52 (best seen at FIG. 5). The communicative cable 105 can be movably disposed between the linear drawer assembly 2 and drawer tray 100. In other embodiments, the communicative cable 105 can be biased to wind around a spool. When the corresponding linear assembly 2 is in an open position, communicative cable 105 unwinds from the spool and extends to the open position of linear assembly 2. When linear assembly 2 is returned to a closed position, communicative cable 105 rewinds around the spool.

When a drawer tray 100 includes a full complement of linear drawer assemblies 2, it forms an entire horizontal row of linearly-extensible drawers in the medication storage and dispensing workstation. The entire drawer tray is then referred to as a "tier" of drawers.

Figure 11A:
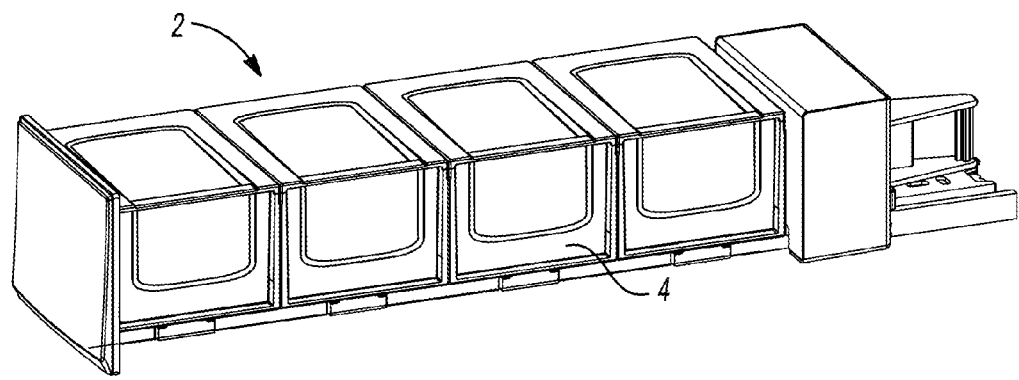
FIG. 11A is a front perspective view of a drawer assembly for a medication storage and dispensing workstation having a plurality of discrete drawer-in-drawer storage modules according to the present disclosure.
Figure 11B:
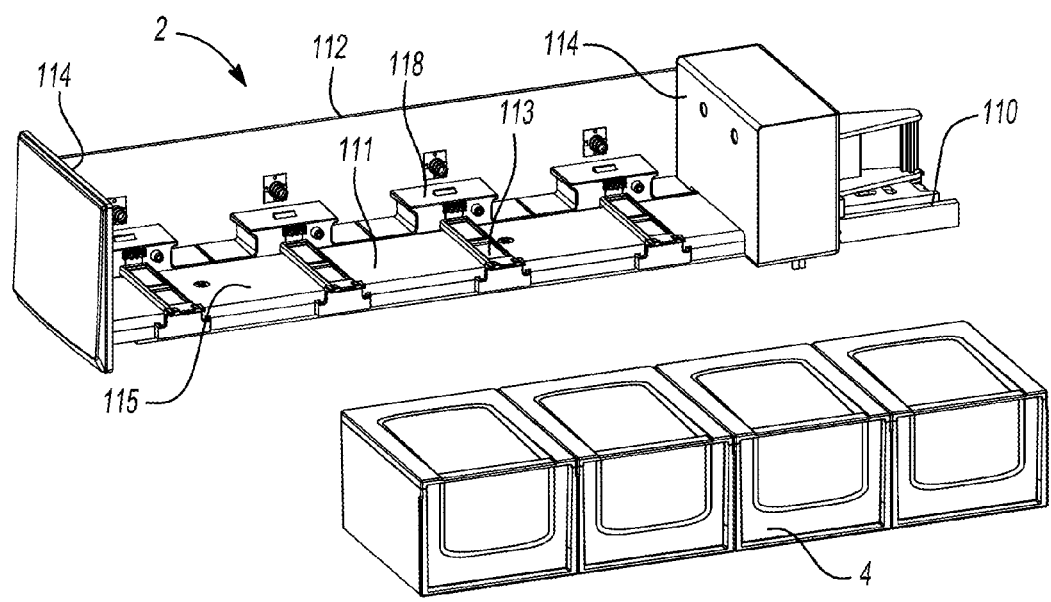
FIG. 11B is a front perspective view of the drawer assembly showing the discrete storage modules detached from the drawer.

Referring now to FIG. 11, each of the storage modules 4 is configured to be removably mounted to a drawer frame 110 of the linear drawer assembly 2. Although four storage modules are shown in the figures, a fewer or greater number of storage modules can be employed. The drawer frame 110 comprises an open platform 115 having a bottom 111, a back wall 112 and two opposing side walls 114. Secured to the bottom 111 of the drawer frame 110 are a plurality of guide rails 113, each of which are intended to correspondingly engage one of the storage modules 4. Each storage module 4 is operable to slidably interface with a corresponding guide rail 113. A compartment latch mechanism 118 is located at an end of the guide rail 113 and adjacent to the back wall 112 of the drawer frame 110. The drawer frame 110 is, in turn, mounted to a drawer slide sub-assembly, which is best seen in FIGS. 10A and 13, such as by fasteners or the like.

Figure 12:
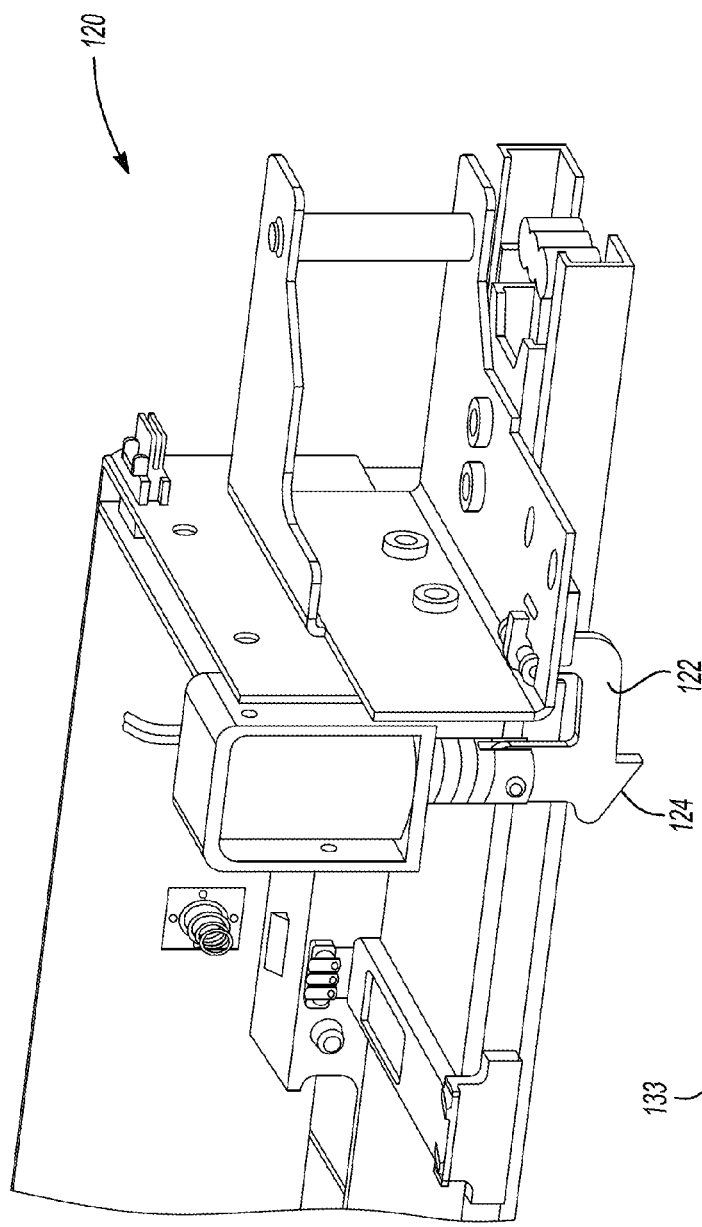
FIG. 12 shows an enlarged partial front perspective view of a rear portion of the drawer assembly having a cover component removed.

As best seen in FIG. 12, the linear drawer assembly 2 includes an in-drawer controller 120. The in-drawer controller 120 can communicate with both a tier controller 50 and a storage module controller 52, as shown, e.g., in FIG. 5, and further described herein. Also included in the linear drawer assembly 2 and in communication with the in-drawer controller 120 is a drawer extension lock 122. The drawer extension lock 122 includes a solenoid or other locking mechanism, and a sensor such as an optical or mechanical switch that can be attached to a drawer catch 124. The drawer catch 124 is pivotable about a pivot axis and can move between a retracted "up" position and an extended "down" position (as viewed in FIG. 12). Alternatively, the drawer catch can comprise a linear actuator, a magnetic or another known electrically or magnetically-actuated mechanism. The drawer catch 124 can be normally biased toward the down position such as by a spring. When the linear drawer assembly 2 is in a fully closed condition, the downward bias can be opposed by the drawer tray 100 on which the linear drawer assembly 2 is mounted. However, when the linear drawer assembly 2 is in a fully extended and opened condition, and the drawer catch 124 can extend beyond the exterior front end of the drawer tray 100, the bias against the drawer catch 124 moves the drawer catch 124 to the extended "down" position such that a shoulder portion of the drawer catch 124 can engage against the front end of the drawer tray 100 and prevent the linear drawer assembly 2 from being moved toward the closed condition. Under the control of the in-drawer controller 120, however, the solenoid can operate to move the drawer catch 124 to the retracted "up" position such that the shoulder portion of the drawer catch 124 is disengaged from the drawer tray 100 and the linear drawer assembly 2 can move toward the closed condition.

Figure 13:
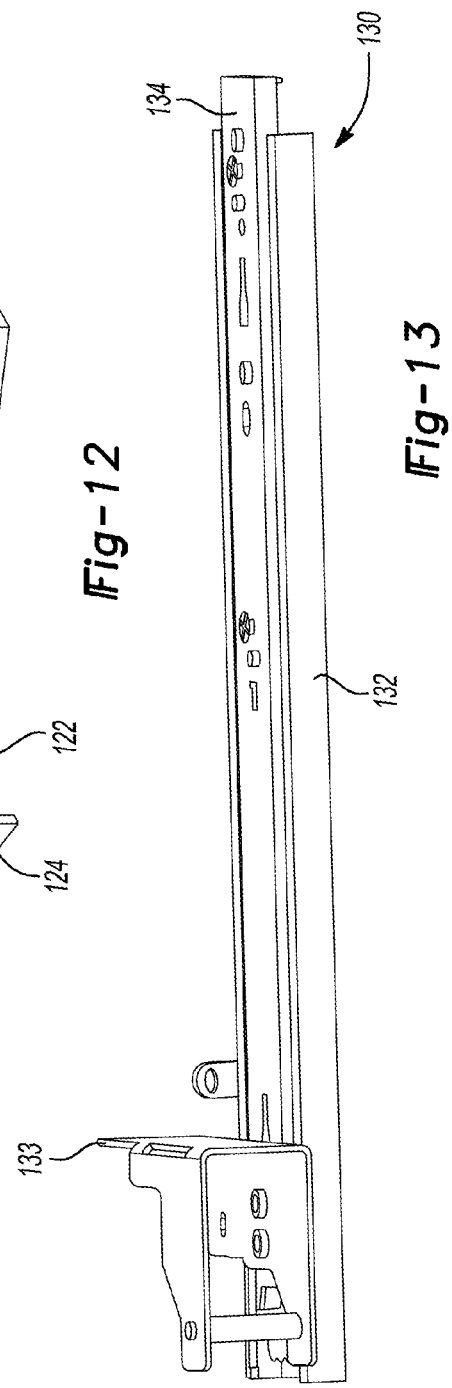
FIG. 13 is a perspective view of a drawer slide component of the drawer assembly.

FIG. 13 shows a more detailed view of the drawer slide sub-assembly 130 of the linear drawer assembly 2. The drawer slide sub-assembly 130 is extensible along a longitudinal axis and is operable to maneuver the linear drawer assembly 2 into and out of the cabinet of the medication storage and dispensing workstation. The drawer slide sub-assembly 130 includes a base rail 132 that is configured for mounting to the drawer tray 100, such as by one or more fasteners, or the like. A slide rail 134 is moveably nested within the base rail 132 and is operable to move linearly relative to the base rail 132 along the longitudinal axis. The drawer frame 110 is attached to the slide rail 134. A latch bracket 133 including a latch bar for engagement with a corresponding linear drawer latch mechanism is included at a rear end of the drawer slide sub-assembly 130.

The storage module latch mechanism can be understood with reference to FIGS. 14 through 18. The storage module latch mechanism 140 comprises a two-stage latch device that can be electronically controlled. The storage module latch mechanism 140 is contained within a housing 141 and includes a first stage latch 142 comprising a lock bolt 148 that is slidably received within a bracket 143, a second stage latch 144 comprising an intermediate bracket 147 that is also slidably received in the bracket 143, and an actuator.

Figure 22:
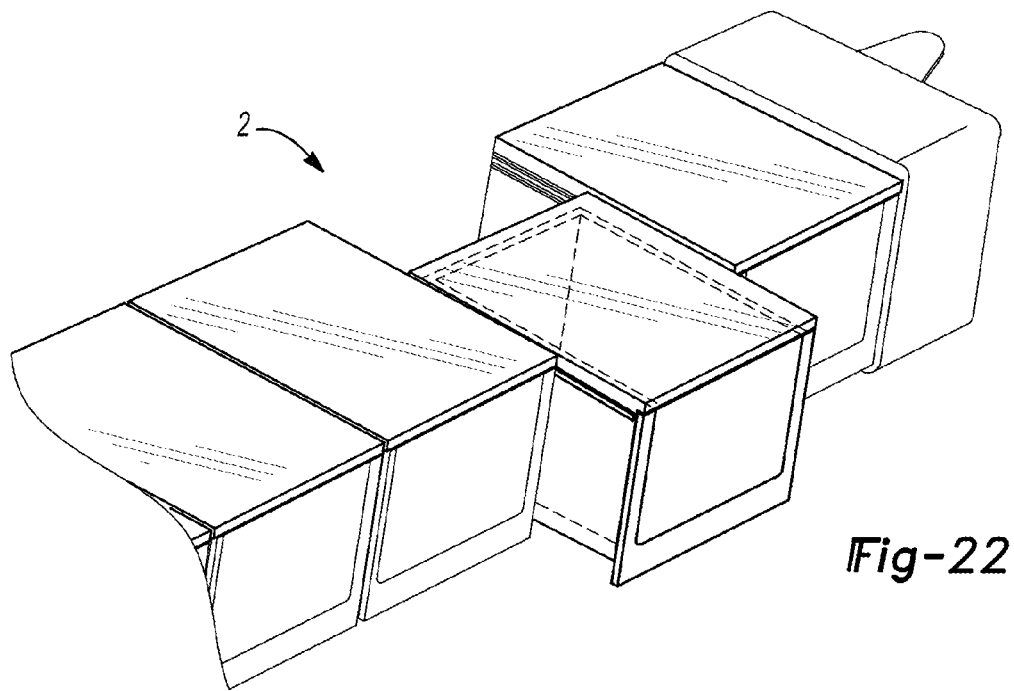
FIG. 22 is a perspective view showing a discrete storage module of the drawer assembly detached from the drawer assembly.

The lock bolt 148 can be normally biased by a spring or other biasing means in an upward direction so as to protrude from an upper surface of the housing 141 in an engagement position. When in the engagement position, the lock bolt 148 can engage a corresponding receiving aperture 192 (best seen in FIG. 19B) in the storage module 4 so as to secure the storage module 4 in place. The intermediate bracket 147 is normally biased by a spring or other biasing means in the same direction as the lock bolt 148. The intermediate bracket 147 can bear against the lock bolt 148 such that movement of the intermediate bracket 147 in the downward direction also results in movement of the lock bolt 148 in the downward direction. Downward movement of the lock bolt 148, however, does not result in movement of the intermediate bracket 147. Therefore, the first stage latch 142 is operable without disturbing the second stage latch 144. The actuator can engage the intermediate bracket 147 to cause it to move in a downward direction and overcome the upward bias against the intermediate bracket 147 and the lock bolt 144. The actuator can comprise a memory metal wire. When the memory metal wire is activated, it pulls downward on the intermediate bracket 147, overcoming the bias against downward movement of the intermediate bracket 147 and the lock bolt 148, and moves the lock bolt 148 to release the storage module 4 from the linear drawer assembly 2. A pin 149 biased in the direction laterally away from the storage module latch mechanism 140, such as by a spring, can eject the storage module 4 after it is released from the storage module latch mechanism 140, as shown in FIG. 22.

The storage module latch mechanism is controlled by the storage module controller. The storage module controller is housed in a base portion of the storage module, as discussed below.

Figure 14:
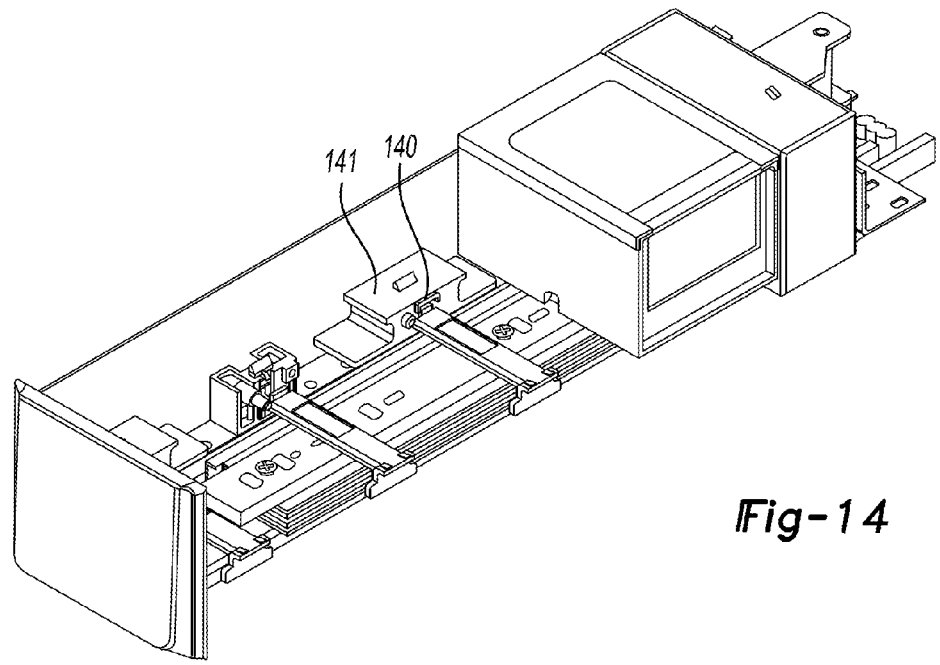
FIG. 14 is a partial perspective view of a portion of the drawer assembly of FIG. 11B having a back wall shown as transparent and showing a latch mechanism for one of the a discrete storage modules with a housing removed.
Figure 15:
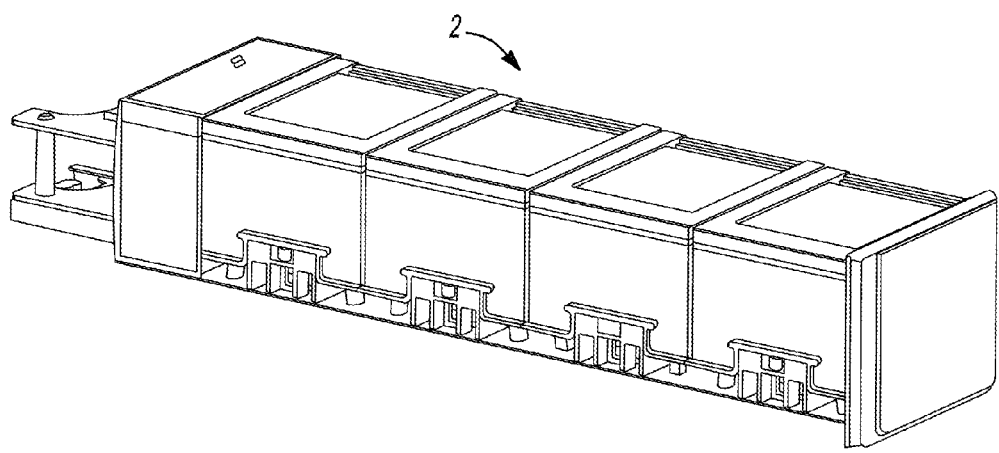
FIG. 15 is a rear perspective view of the drawer assembly having a back wall shown as transparent.
Figure 16:
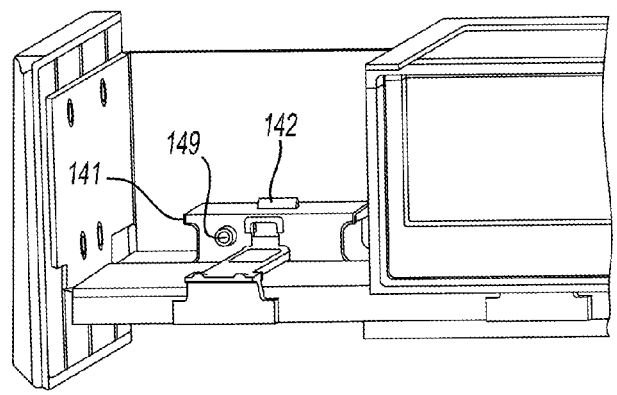
FIG. 16 is a perspective view of a latch mechanism for one of for the a discrete storage modules in a drawer assembly.
Figure 17:
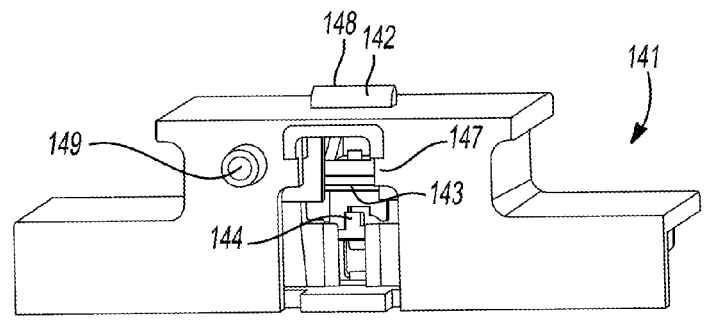
FIG. 17 is a perspective view of a latch mechanism for one of the discrete storage modules.
Figure 18:
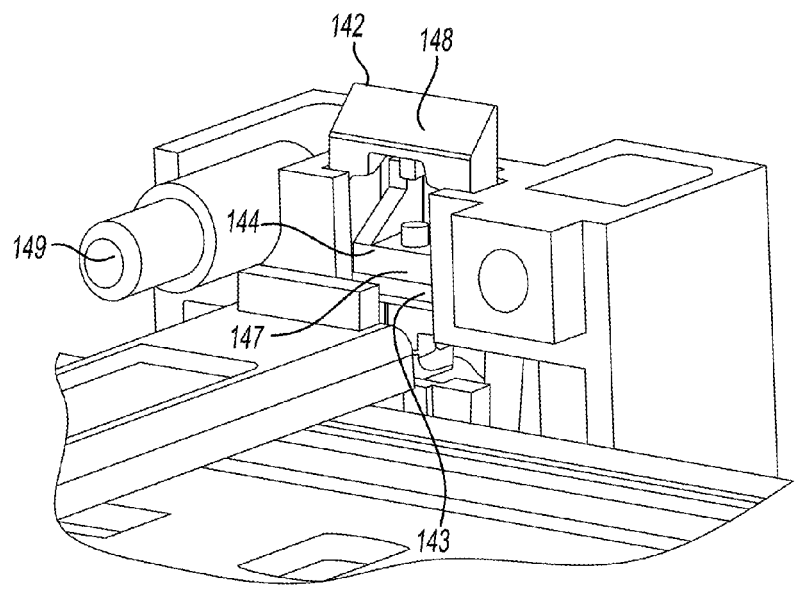
FIG. 18 is a perspective view of a latch mechanism for the discrete storage modules having the housing removed to reveal additional components of the mechanism.
Figure 19A:
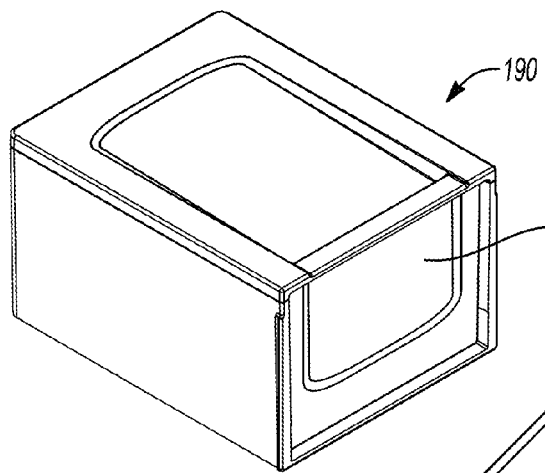
FIG. 19A is front perspective view of a discrete storage module.
Figure 19B:
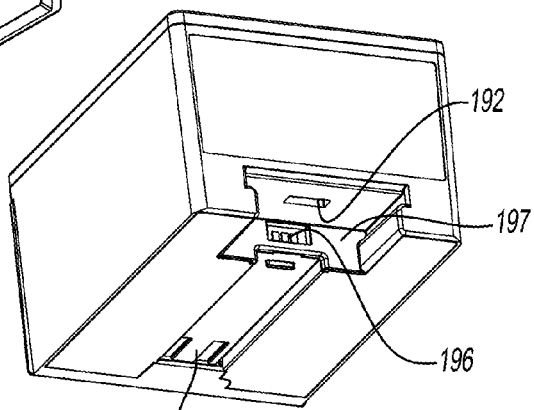
FIG. 19B is a rear perspective view of a discrete storage module.
Figure 19C:
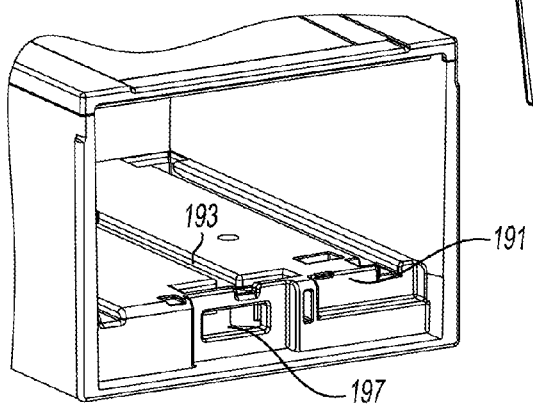
FIG. 19C is a front perspective view of a discrete storage module having the lateral drawer removed.
Figure 19D:
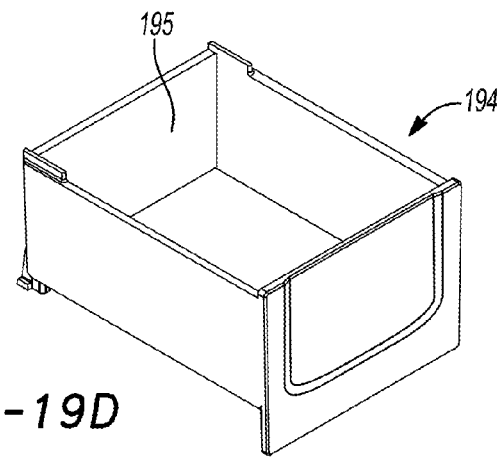
FIG. 19D is a perspective view of a lateral drawer for the discrete storage module.
Figure 20A:
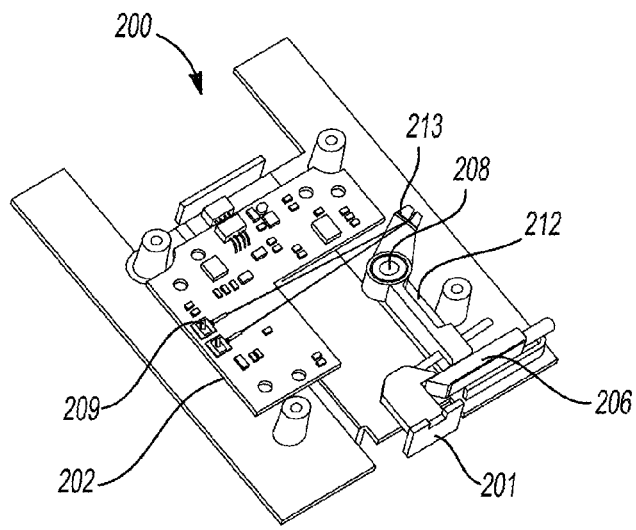
FIGS. 20A, 20B and 20C show perspective views of the lateral drawer latch mechanism and controller for a discrete storage module.
Figure 20B:
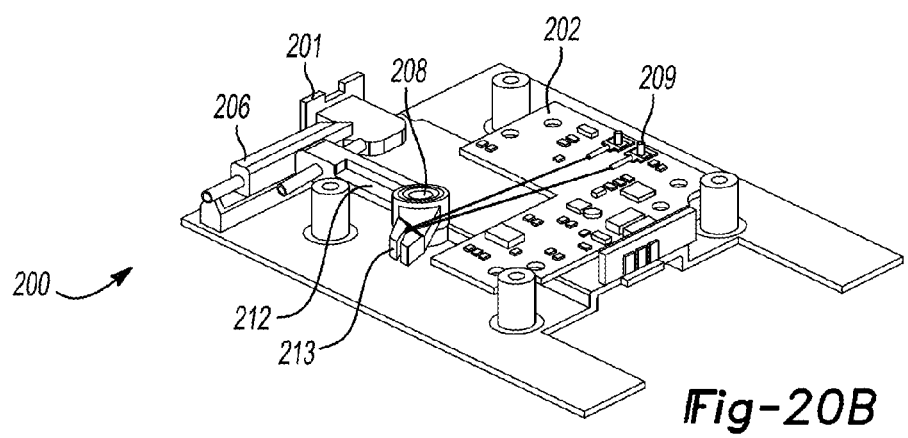
Figure 20C:
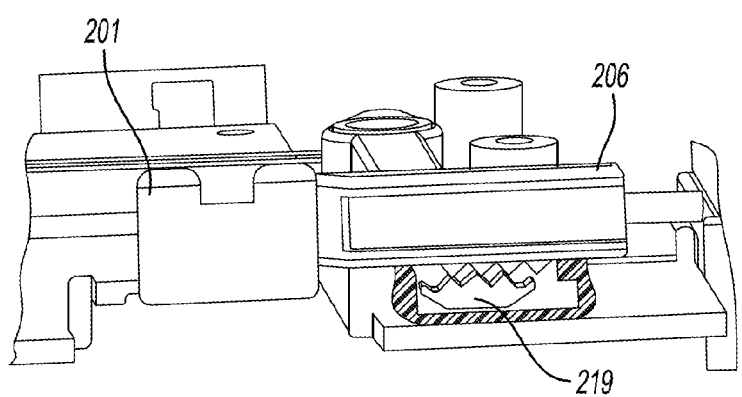
Figure 21:
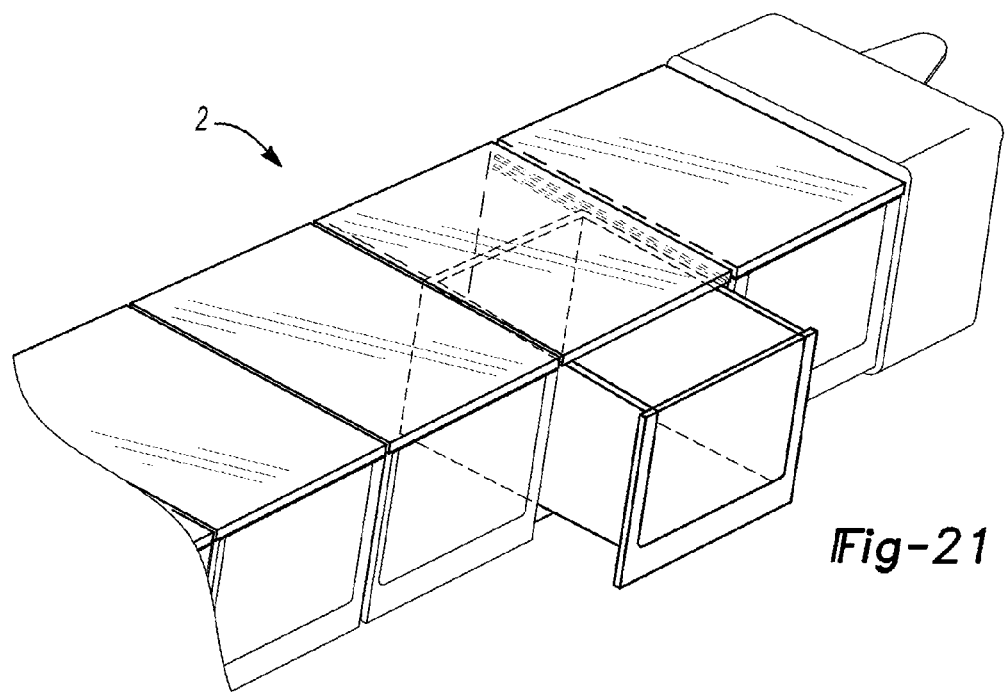
FIG. 21 is a perspective view showing a lateral drawer of a discrete storage module of the drawer assembly in an open position.

FIGS. 19A-19D and 20A-20C show the storage module in greater detail. As shown in the figures, the storage module comprises a housing 190, a lateral drawer 194 slidably received within the housing, a lateral drawer latch mechanism 200, and a storage module controller 202. The housing 190 and lateral drawer 194 are best seen in FIGS. 19A-19D. The housing 190 includes an opening 197 at a bottom rear end that is shaped to accommodate a nesting-type interface with the storage module latch mechanism 140, as can be seen in FIG. 14. The opening 197 incorporates a receiving aperture 192 for engaging the lock bolt 148 of the storage module latch mechanism 140, as previously described. In addition, the bottom of the housing includes a channel 198 for accommodating a slidable interface with a corresponding guide rail 113 as previously indicated. The lateral drawer 194 is slidable between a closed condition (as shown in FIG. 19A) and an opened condition (as seen in FIG. 21). As shown in FIG. 19C, the interior bottom surface 191 of the housing 190 includes channels 193 that receive corresponding extension portions on the bottom of the lateral drawer and guide the lateral drawer 194 relative to the housing 190 as it moves between the opened and closed conditions. As seen in FIG. 19D, the lateral drawer 194 provides an interior storage 195 space for items contained in the medication storage and dispensing workstation. As best seen in FIG. 19C, which shows the storage module 4 having the lateral drawer 194 removed for purposes of illustration, a front end of the housing includes an opening 197 through which a latch hook 201 attached to the lateral drawer (shown in FIGS. 20A-20C) can be received in the lateral drawer latch mechanism 200.

The storage module 4 also includes a lateral drawer latch mechanism 200 and a storage module controller 202 that are contained within a base portion of the housing 190 of the storage module 4. FIGS. 20A-20C show the lateral drawer latch mechanism 200 in greater detail. The lateral drawer latch mechanism 200 comprises a two-stage latch device that can be electronically controlled. The lateral drawer latch mechanism 200 includes a first stage latch comprising a lock bolt 206 that is slidably received within a channel formed in the base portion of the housing 190 of the storage module 4 near the front end of the storage module; a second stage latch comprising a pivot bracket 208 that is pivotally mounted to the base portion and is received in a slot in the lock bolt; and an actuator 209.

The lock bolt 206 can be normally biased by a spring or other biasing means in a direction so as to extend inward toward the longitudinal center of the housing 190 in an engagement position. When in the engagement position, the lock bolt 206 can engage the latch hook 201 attached to the lateral drawer 194 so as to secure the lateral drawer 194 in the closed condition. The pivot bracket 208 comprises a first arm 212 having a first end and a second arm 213 having a second end. At the location where the first and second arms join together, the pivot arm is pivotally mounted to the base portion of the housing 190. The first arm 212 is normally biased by a spring or other biasing means in the same direction as the lock bolt 206 such that it bears against a post that serves to prevent further movement of the first arm 212 in an inward direction. The first end of the first arm 212 is received in the elongated slot in the lock bolt 206 and can bear against the outward side of the slot such that movement of the pivot bracket 208 in an outward direction (away from the longitudinal center of the housing) also results in movement of the lock bolt 206 in the outward direction. Outward movement of the lock bolt 206, however, does not result in movement of the pivot bracket 208 since the elongated slot provides clearance on the inward side of the slot between the lock bolt 206 and the pivot bracket 208 allowing relative movement of the lock bolt 206 in the outward direction. Consequently, the first stage latch is operable without disturbing the second stage latch.

The actuator 209 can engage the second end of the second arm 213 of the pivot bracket 208 so as to cause the first end of the first arm 212 to overcome the bias against the bracket arm and the lock bolt 206 and move in an outward direction. The actuator 209 can comprise a memory metal wire. When the memory metal wire is activated, it pulls inward on the second end of the second arm 213, causing the first arm 212 and the lock bolt 206 to move in the outward direction and release the latch hook 201 of the lateral drawer 194. Moreover, the lateral drawer 194 can be biased in the direction laterally away from the lateral drawer latch mechanism 200, such as by a spring interposed between the housing and the lateral drawer, to eject the lateral drawer 194 after it is released from the lateral drawer latch mechanism 200, such as is illustrated in FIG. 21.

Still further, as shown in FIG. 20C, the storage module includes an impact lock to help prevent the unintended disengagement of the lateral drawer latch mechanism 210 and subsequent opening of the lateral drawer 194. For example, in cases where the storage module 4 may be subjected to an impact or shock force, there is the potential that the lock bolt 206 of the lateral drawer latch mechanism 200 could disengage from the latch hook 201 as a result of inertial forces overcoming the bias that maintains the lateral drawer latch mechanism 200 engaged. The impact lock comprises a floating wedge member 219 that is operable to engage the lock bolt 206 under conditions where impacts or shocks may occur. The wedge member 219 is positioned in a slot located beneath the lock bolt 206. The slot captures the wedge member 219 limiting its movement horizontally, but allowing for slight movement vertically upward. Opposing angled surfaces on the wedge member 219 and the slot produce vertical movement of the wedge member 219 when subjected, for example, to a shock force. The wedge member 219 includes a serrated or toothed upper surface that opposes a corresponding serrated or toothed lower surface formed on the lock bolt 206. Under the influence of a shock force, then, the teeth of the floating wedge member 219 can engage the teeth of the lock bolt 206, thereby inhibiting movement of the lock bolt 206 that could result in the lock bolt 206 disengaging from the latch hook 201.

Figure 23:
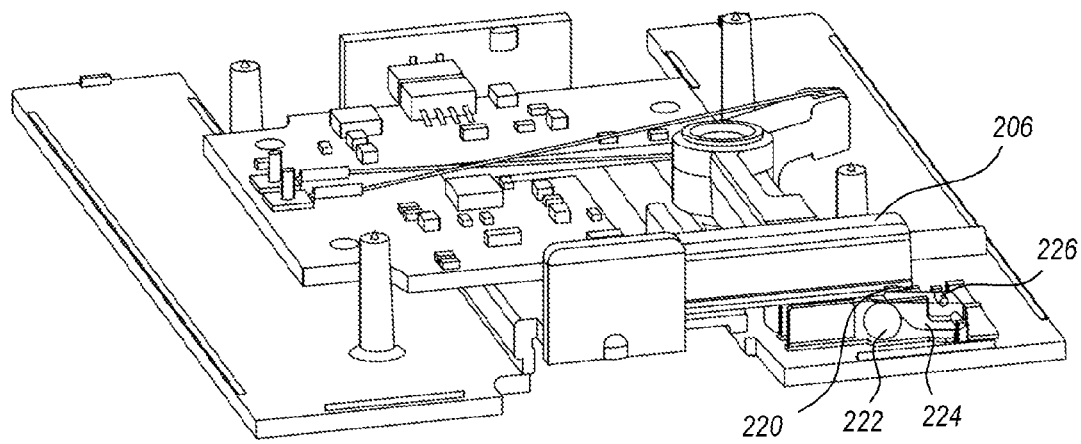
FIG. 23 is a perspective view of the lateral drawer latch mechanism and controller for a discrete storage module.
Figure 24:
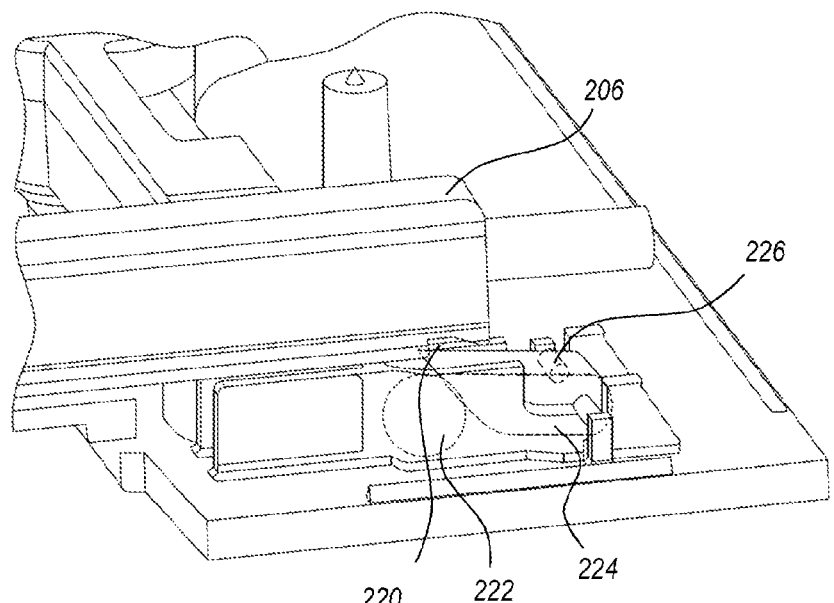
FIG. 24 is a partial perspective view of the lateral drawer latch mechanism.

An alternative impact lock is shown in FIGS. 23 and 24. This impact lock uses a small ball bearing 222 as a motive force to push a lock pawl 224 into engagement with a slot 220 in the lock bolt 206. The lock pawl 224 pivots on a pin 226 and catches the slot 220 to prevent the opening of the lock bolt 206 under the influence of an impact or shock force.

Figure 5:
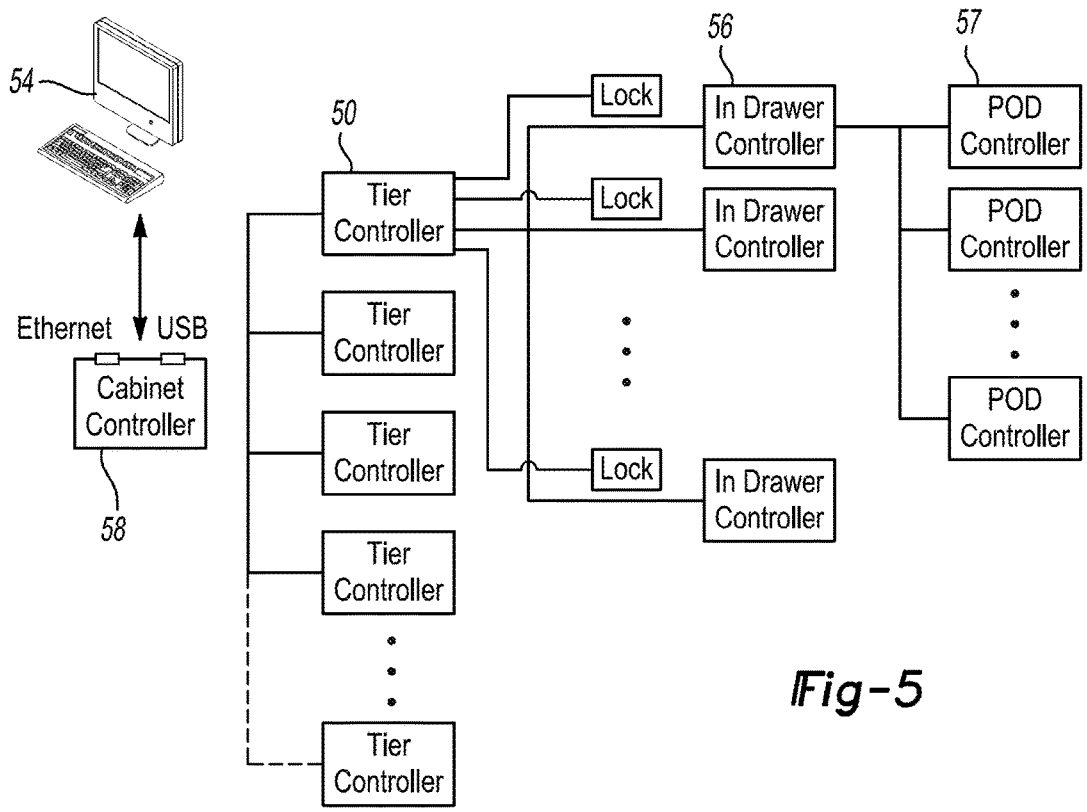
FIG. 5 is a schematic block diagram depicting an exemplary control scheme for a medication storage and dispensing workstation incorporating discrete drawer-in-drawer storage modules according to the present disclosure.

Turning to FIGS. 5-9, several simplified schematic block diagrams are illustrated. FIG. 5, for example, is a simplified schematic block diagram generally showing an overview of the systems architecture for an exemplary medication storage and dispensing workstation according to the present disclosure. As shown, the system can include a control computer 54 that communicates with a workstation network system. The workstation network system can include at least a workstation controller 58, a plurality of tier controllers 50, a plurality of in-drawer controllers (or "drawer controllers") 56, a plurality of storage module controllers 52, and a plurality of pod controllers 57. The workstation controller 58 is sometimes referred to as a "cabinet controller." The workstation controller 58 can be connected to the plurality of tier controllers 50, with each tier controller 50 can be associated with a single horizontal row of linear drawer assemblies 2 in the workstation. In communication with each tier controller 50 can be the plurality of in-drawer controllers 56 and a plurality of linear drawer latch mechanisms 106 associated with each of the plurality of linear drawer assemblies 2. Each in-drawer controller 56 can also be connected to a plurality of storage module controllers 52, each housed within a storage module 4 of the linear drawer assembly 2. In communication with each in-drawer controller 56 can be a plurality of pod controllers 57.

The control computer 54 can comprise a general purpose computer operating under the control of operating system software (e.g., Microsoft Windows®) and hardware drivers that can bridge the communications between a medication inventory management software application program running on the control computer and the controllers of the workstation network system. When the application software is running on the control computer 54, for example, the control computer 54 can communicate with the workstation network system, such as through an Ethernet communications port or a USB communications port. Some of the functions/operations that can be performed through the control computer 54 and/or the application software can include: determining how many cabinet controllers 58 are attached to the system; assigning addresses to each cabinet controller 58; mapping the cabinet network system in each cabinet, including the location, identification, revision levels, etc. of any components; communicating with and controlling each component in the workstation network system; managing firmware upgrades to system hardware components; and running system diagnostics.

A simplified schematic block diagram for the workstation controller 58 is shown in FIG. 7. The workstation controller 58 can perform functions/operations that include: self-identification; upstream communication functions; tier controller communication and control functions; assignment of tier addresses; and storage module controller communication and control functions.

A simplified schematic block diagram for the tier controller 50 is shown in FIG. 8. The tier controller 50 can perform functions/operations that include: self-identification; upstream communication functions; in-drawer controller communication and control functions; assignment and management of assigned cabinet drawer addresses (ACDA) for each in-drawer controller; acting on operating commands addressed to the ACDAs; providing reloading operating instructions; controlling operation of the linear drawer latch mechanism.

The in-drawer controller 56 can perform functions/operations that include: self-identification; upstream communication functions; storage module communication and control, including identifying the number of available storage module locations (i.e., maximum number of locations in the linear drawer), the identity and/or number of occupied storage module locations, the unique information for each storage module, such as ID, size, firmware revision, tamper state, etc.; assign and manage assigned storage module addresses for each storage module; controlling operation of the command received directed to that storage module address; determining state of lateral drawers; and enabling closure of the linear drawer.

The storage module controller 52 can perform functions/operations including: self-identification; upstream communication functions; provide indication via an indicator of the storage module; actuate and/or detect the opening of the lateral drawer; actuate and/or detect the ejection the storage module from the linear drawer assembly; and tamper monitoring.

The pod controller 57 can perform options including: self-identification; upstream communication functions; actuate and/or detect the opening of the storage module drawer; and tamper monitoring.

Figure 6:
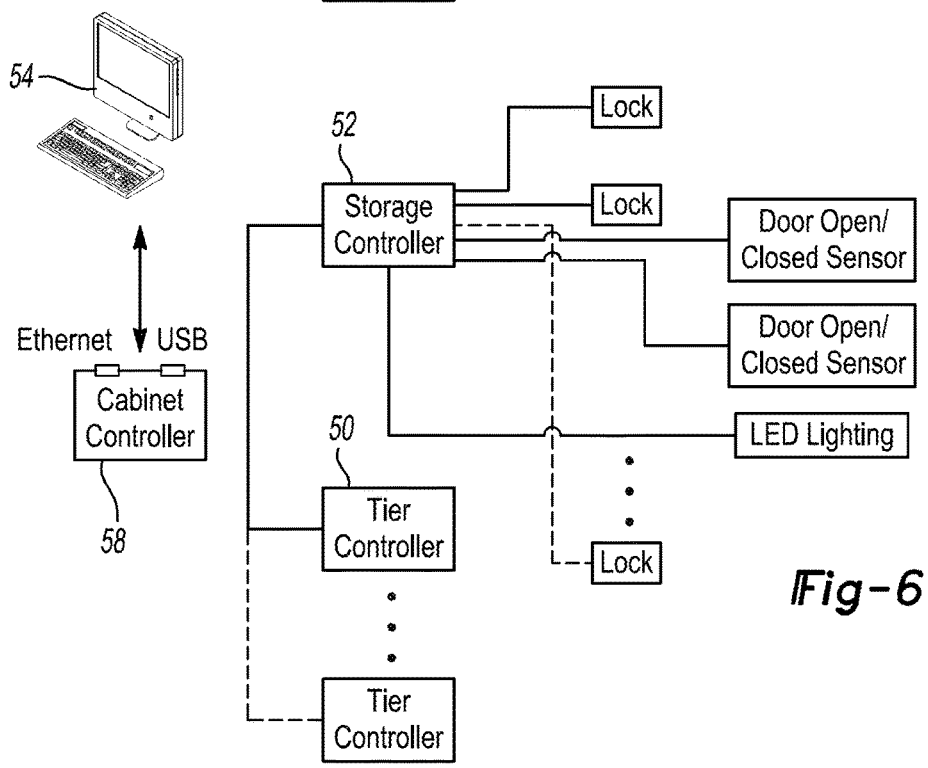
FIG. 6 is a schematic block diagram depicting an exemplary control scheme for a medication storage and dispensing workstation incorporating discrete drawer-in-drawer storage modules and a storage cabinet including cabinet doors according to the present disclosure.
Figure 9A:
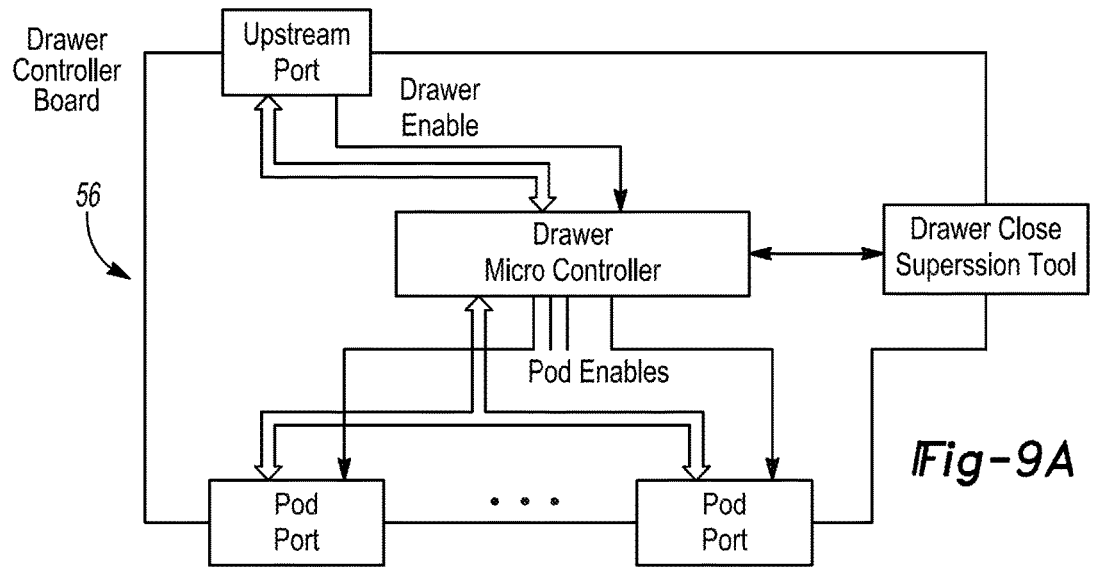
FIG. 9A is a schematic block diagram showing a storage drawer controller for use with a medication storage and dispensing workstation of the present disclosure.
Figure 9B:
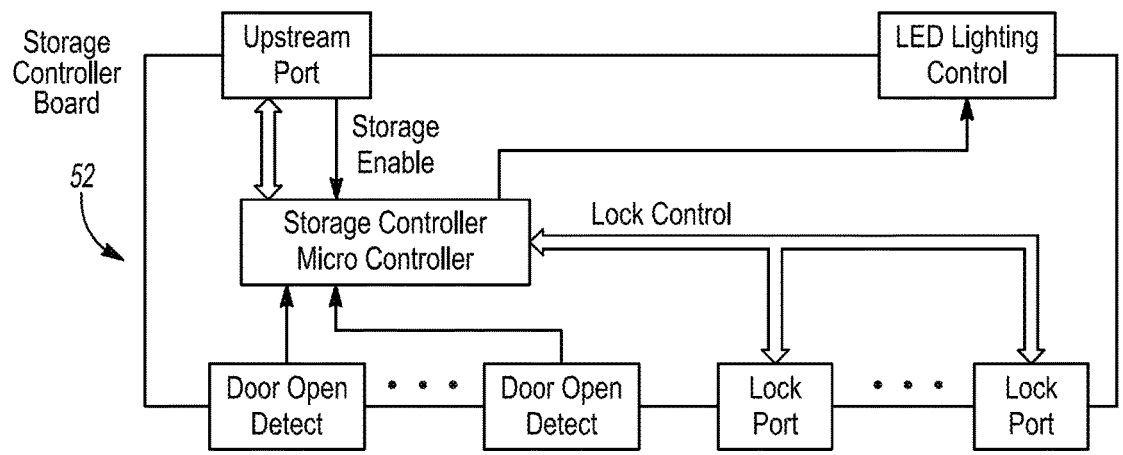
FIG. 9B is a schematic block diagram showing a storage controller for use with a medication storage and dispensing workstation of the present disclosure.
Figure 9C:
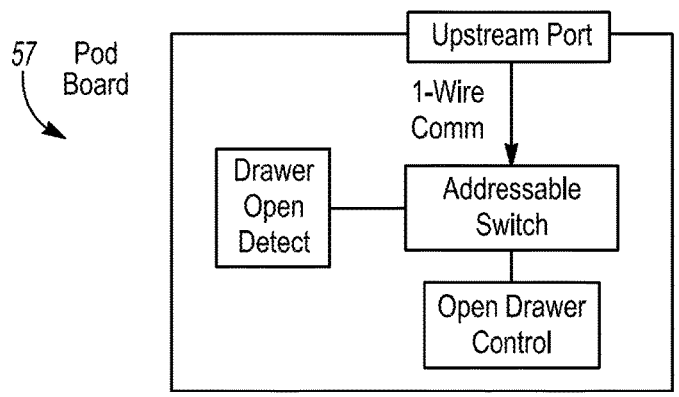
FIG. 9C is a schematic block diagram showing a pod controller for use with a medication storage and dispensing workstation of the present disclosure.

FIG. 6 shows a simplified schematic block diagram generally depicting an overview of the systems architecture for another exemplary medication storage and dispensing workstation according to the present disclosure. FIG. 9A shows a simplified schematic block diagram for the drawer controller 56 of FIG. 6. FIG. 9B shows a simplified schematic block diagram for the storage controller for the workstation of FIG. 6. FIG. 9C shows a simplified schematic block diagram for the pod controller 57 for the workstation of FIG. 6.

A process for using the workstations of the present disclosure begins with an authorized healthcare professional gaining access to the workstation according to the protocols for the facility. For example, the healthcare professional provides appropriate credentials and access is permitted to the workstation.

Once access to the workstation is accomplished, the authorized healthcare professional can obtain the patient specific prescription drug information for the patient(s) under that professional's care, such as from a centralized medication inventory management system. The prescription drug information for the patient can be queued at the workstation. The process of obtaining patient specific prescription drug information can be repeated for each of the patients that the healthcare professional will round. The workstation then enables access by the authorized healthcare professional to the drawer(s) and storage module(s) containing the specific medication(s) prescribed to patient.

The healthcare professional can then retrieve the medication(s) from the workstation and record the activity according to the facility's protocol. The drawer(s) on the workstation are then closed and locked.

The linear drawer assemblies and/or storage modules can be organized within a workstation in a variety of ways, such as by medication type, by one or more medications to be delivered to at least one specific patient, or by a specific user, such as a health care provider.

It can also be appreciated that an indicator, such as an LED light, which is activated in response to a request for access to a specific storage module, thereby indicating to the user which storage module should or can be accessed, can be included.

The lateral drawer can automatically open in response to a user request for the medication or medical supply that is contained in the storage module, the remaining storage modules being locked so as to restrict access into any other storage module except the one having the requested item.

The linear drawer assembly may automatically move slidably outward only partially. A user can open the linear drawer assembly to its fully open and extended position. The drawer assembly can latch upon reaching the fully extended position. Upon access to the desired storage module, the latch can release, thereby enabling the opened linear drawer assembly to be closed.

Further, the opening of or access to a storage module can automatically record in the application software. In certain embodiments, the application software can record the access and/or provide feedback to a user that the correct or incorrect storage module was accessed, depending on specifications. This indication can take the form of an alert so as to inform a user that an incorrect storage module was selected or accessed. The alert can be transferred to someone other than the user or recorded in a data record. In certain instances, the access record can be associated with the taking of inventory.

In one exemplary embodiment, a healthcare professional could enter specifications into the application software running on the control computer that has inventoried the items contained within a storage device containing at least one drawer assembly according to the present disclosure. The host control module communicates to a transceiver located within the housing, indicating to the transceiver which storage module on which drawer assembly contained the desired item. The transceiver would actuate the actuator juxtaposed to such drawer assembly, thereby causing the drawer assembly to linearly slide outward from the housing. The transceiver would next actuate the actuator in direct connection with the storage module, thereby causing the storage module to travel laterally from the linear direction the drawer assembly had slidably traveled. The user would collect the desired item from the open storage module. The removal of the item would be indicated to the host control module, with the host control module thereby inventorying the item's extraction. The user would then push the storage module back into a closed position, then push the drawer assembly back into the housing. The user may then request a new specification as described above, or may make several specifications initially, wherein the corresponding drawer assemblies and storage module would open sequentially or all at once.

The storage modules may be interchangeably removable from the linear drawer assemblies, thereby allowing depleted storage modules to be quickly exchanged with fully stocked storage modules. Alternatively, the storage modules may be interchanged so as to exchange the items contained in the storage device. Alternatively, the storage modules may be interchangeably removed, to provide a means of easily and securely reconfiguring the inventory locations and quantities within a workstation. In these respects, the storage modules can include or be associated with an identification mechanism, such as a label, code, magnetic, or electronic, or radio frequency device, for example. The identification mechanism can contain information about the identity of the storage module, the items contained therein, and/or its associated workstation. This information can be updated, tracked, checked, and re-confirmed during the entire process for the storage and distribution of items from the workstation, for example, from a centralized pharmacy to a nurses' station in a hospital ward to a patient. Exemplary identification mechanisms can include color codes, serial numbers, bar codes, RFID devices, micro-circuits, and the like such that each storage module is uniquely identified.

Although the storage modules are shown as generally occupying a single position in the linear drawer assembly, it should be understood that the sizes of the storage modules can be varied between different linear drawer assemblies, as well as within a single linear drawer assembly. For example, the storage module "pods" can alternatively be sized to occupy one, two, three or more positions within the linear drawer assembly, and that these pods can be mixed and matched in combinations between different linear drawer assemblies in a workstation.

As can be appreciated, a workstation according to the principles of the present disclosure can incorporate drawer assemblies that are organized vertically rather than horizontally, such that the storage modules are disposed in a vertical manner.

A workstation incorporating a linear drawer assembly according to the present disclosure has an efficiency over other known workstations. Known medical dispensary apparatuses require opening drawers that are bulky and not conducive to a small, enclosed area as may be encountered in a crowded hallway. The linear drawer assemblies with discrete storage modules according to the present disclosure, however, do not require a drawer spanning the entire width of the dispensary apparatus to extend from the apparatus, thereby allowing the user to utilize the workstation in a smaller area.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medication storage and dispensing workstation for use in a medication management system administering the inventory and distribution of pharmaceuticals and medical supplies in a healthcare environment comprising:
   a linear drawer assembly having a plurality of discrete, removable, storage modules for containing medications and/or other medical supplies;
   wherein the storage modules are arranged in a linear array extending longitudinally along the travel path of the linear drawer assembly; and
   wherein each storage module comprises a horizontal drawer that is extendable laterally relative to the linear arrangement of the storage modules, wherein at least one of the storage modules includes a lock positioned to removably secure the storage module to the linear drawer assembly.

2. The medication storage and dispensing workstation of claim 1, wherein the storage modules are individually removable from the linear drawer assembly.

3. The medication storage and dispensing workstation of claim 1 further comprising:
   a control computer; and
   a workstation network system comprising a workstation controller, at least one tier controller, at least one in-drawer controller, and a plurality of storage module controllers;
   wherein the workstation controller is in communication with the tier controller;
   wherein the tier controller is in communication with the in-drawer controller and a linear drawer latch mechanism associated with the linear drawer assembly; and
   wherein the in-drawer controller is in communication with a plurality of storage module controllers.

4. The medication storage and dispensing workstation of claim 1, wherein said linear drawer assembly is removably connected to said workstation via a two-stage lock.

5. The medication storage and dispensing workstation of claim 1, wherein said plurality of storage modules are removably secured to said linear drawer assembly via a two-stage lock.

6. The medication storage and dispensing workstation of claim 3, wherein each said storage module has a unique identifier.

7. The medication storage and dispensing workstation of claim 6, wherein each said storage module is identified by a said unique identifier to determine a particular storage module.

8. The medication storage and dispensing workstation of claim 7, wherein said linear assembly opens to allow access to said particular storage module.

9. A medication storage and dispensing workstation for use in a medication management system administering the inventory and distribution of pharmaceuticals and medical supplies in a healthcare environment comprising:
   at least a frame assembly comprised of at least a linear drawer assembly, wherein said linear drawer assembly is comprised of at least two removable storage modules arranged in a linear array longitudinally along the travel path of the linear drawer assembly;
   wherein each storage module defines a volume;
   wherein each storage module is removable laterally relative to the linear arrangement of the drawer assembly;
   wherein each storage module is removable without affecting the volume defined by another storage module; and
   wherein each storage module comprises a drawer that is extensible laterally horizontally relative to the travel path of the linear drawer assembly.

10. The medication storage and dispensing workstation according to claim 9, wherein the storage modules are individually removable from the linear drawer assembly.

11. The medication storage and dispensing workstation according to claim 9, further comprising:
    a control computer; and
    a workstation network system comprising a workstation controller, at least one tier controller, at least one in-drawer controller, and a plurality of storage module controllers;
    wherein the workstation controller is in communication with the tier controller;
    wherein the tier controller is in communication with the in-drawer controller and a linear drawer latch mechanism associated with the linear drawer assembly; and
    wherein the in-drawer controller is in communication with a plurality of storage module controllers.

12. The medication storage and dispensing workstation of claim 9, wherein said linear drawer assembly is removably connected to said workstation via a two-stage lock.

13. The medication storage and dispensing workstation of claim 9, wherein said plurality of storage modules are removably secured to said linear drawer assembly via a two-stage lock.

14. The medication storage and dispensing workstation of claim 11, wherein each said storage module has a unique identifier.

15. The medication storage and dispensing workstation of claim 14, wherein each said storage module is identified by a said unique identifier to determine a particular storage module.

16. The medication storage and dispensing workstation of claim 15, wherein said linear assembly opens to allow access to said particular storage module.

17. The medication storage and dispensing workstation of claim 1, wherein each said storage module has an impact lock.

18. The medication storage and dispensing workstation of claim 9, wherein each said storage module has an impact lock.

19. A medication storage and dispensing workstation for use in a medication management system administering the inventory and distribution of pharmaceuticals and medical supplies in a healthcare environment comprising:
    a drawer assembly linearly movable between an open position and a closed position along a longitudinal axis, the drawer assembly comprising a plurality of individual, self-contained storage modules each defining a volume for containing medications and/or other medical supplies, the plurality of storage modules being arranged in a one-dimensional array that is parallel to the longitudinal axis;

wherein each storage module includes a drawer that is extensible generally horizontally and generally in a direction perpendicular to the longitudinal axis; and wherein each storage module is independently removable from the drawer assembly and without affecting the volume defined by another storage module.

20. The medication storage and dispensing workstation of claim 19, wherein each storage module is removable laterally relative to the linear arrangement of the drawer assembly.

21. The medication storage and dispensing workstation of claim 19, wherein said linear drawer assembly is removably secured to said workstation via a two-stage lock.

22. The medication storage and dispensing workstation of claim 19, wherein each of the plurality of storage modules is removably secured to the linear drawer assembly by a storage module latch comprising a first two-stage lock.

23. The medication storage and dispensing workstation of claim 22, wherein the storage module latch comprises a first stage latch comprising a first lock bolt that is slidably received within a first bracket, a second stage latch comprising an intermediate bracket that is also slidably received in the first bracket, and a first actuator.

24. The medication storage and dispensing workstation of claim 19, wherein each storage module further comprises a lateral drawer latch.

25. The medication storage and dispensing workstation of claim 24, wherein the lateral drawer latch comprises:
 a second two-stage lock comprising:
 a second, first stage latch comprising a second lock bolt that is slidably received within the storage module,
 a second, second stage latch comprising a pivotally mounted bracket that is received in a slot in the second lock bolt, and a second actuator.

26. The medication storage and dispensing workstation of claim 25, wherein each said storage module comprises an impact lock.

27. The medication storage and dispensing workstation of claim 26, wherein the impact lock comprises a wedge member that engages the second lock bolt when the storage module is subjected to an impact force.

28. The medication storage and dispensing workstation of claim 27, wherein the impact lock further comprises:
 a slot located beneath the lock bolt, the wedge member being positioned in the slot;
 wherein the wedge member comprises a first portion and the second lock bolt comprises a second portion operable to engage the first portion; and
 wherein the wedge member inhibits movement of the second lock bolt when the first portion engages the second portion.

29. The medication storage and dispensing workstation of claim 28, wherein the slot captures the wedge member so as limit its movement horizontally while allowing movement vertically upward;
 wherein the first portion of the wedge member and the second portion of the second lock bolt each comprise serrations;
 wherein engagement of the serrations inhibits movement of the second lock bolt.

30. The medication storage and dispensing workstation of claim 26, wherein the impact lock comprises a ball bearing and a lock pawl that engages the second lock bolt when the storage module is subjected to an impact force.

31. The medication storage and dispensing workstation of claim 19 further comprising:
 a control computer; and
 a workstation network system comprising a workstation controller, at least one tier controller, at least one in-drawer controller, and a plurality of storage module controllers;
 wherein the workstation controller is in communication with the tier controller;
 wherein the tier controller is in communication with the in-drawer controller and a linear drawer latch mechanism associated with the linear drawer assembly; and
 wherein the in-drawer controller is in communication with a plurality of storage module controllers.

32. The medication storage and dispensing workstation of claim 31, wherein each said storage module is identified by a said unique identifier to determine a particular storage module;
 wherein the unique identifier comprises one of a label, a color code, a bar code, a serial number, a magnetic device, an electronic device, and a radio frequency device.

33. The medication storage and dispensing workstation of claim 32, wherein the identifier comprises information about one of the identity of the storage module and an item contained within the storage module.

34. The medication storage and dispensing workstation of claim 32, wherein said linear assembly opens to allow access to said particular storage module.

* * * * *